United States Patent
Iiyama et al.

(10) Patent No.: US 8,480,786 B2
(45) Date of Patent: Jul. 9, 2013

(54) METHOD OF MEASURING INFORMATION FOR ADSORPTION ISOSTERE CREATION, ADSORPTION ISOSTERE CREATION METHOD, ADSORPTION HEAT CALCULATION METHOD, COMPUTER PROGRAM, AND MEASUREMENT SYSTEM

(75) Inventors: Taku Iiyama, Nagano (JP); Kazuyuki Nakai, Osaka (JP)

(73) Assignees: Shinshu University (JP); Bel Japan, Inc. (JP)

( * ) Notice: Subject to any disclaimer, the term of this patent is extended or adjusted under 35 U.S.C. 154(b) by 275 days.

(21) Appl. No.: 12/953,657

(22) Filed: Nov. 24, 2010

(65) Prior Publication Data

US 2011/0120301 A1    May 26, 2011

(30) Foreign Application Priority Data

Nov. 24, 2009   (JP) .................................. 2009-266783

(51) Int. Cl.
B01D 53/02 (2006.01)
G01N 5/02 (2006.01)

(52) U.S. Cl.
USPC .......................... 95/15; 95/23; 95/90; 96/109

(58) Field of Classification Search
USPC .............. 95/14, 15, 23, 90; 96/109, 110, 112, 96/113
See application file for complete search history.

(56) References Cited

U.S. PATENT DOCUMENTS

| | | | |
|---|---|---|---|
| 6,391,092 B1 * | 5/2002 | Shen et al. ....................... | 95/120 |
| 6,595,036 B1 * | 7/2003 | Nakai .......................... | 73/19.05 |

FOREIGN PATENT DOCUMENTS

JP    2007-64731 A    3/2007

OTHER PUBLICATIONS

Shen et al., "Isosteric study of sorption thermodynamics of single gases and multi-component mixturess on microporous materials", 1998, Microporous and Mesoporous Materials 22, pp. 237-249.*
Sircar et al., "Isosteric Heat of Adsorption: Theory and Experiment", 1999, J. Phys. Chem. B 103, pp. 6539-6546.*
Czanderna et al., "Surface studies with the vacuum microbalance", Thermochimica Actra, Elsevier Science Publishers, Amsterdam, NL, vol. 24, No. 2, Jun. 1, 1978, pp. 345-358.
De Lange R S A et al., "Analysis and theory of gas transport in microporous sol-gel derived ceramic membranes", Journal of Membrane Science, Elsevier Scientific Publ. Company. Amsterdam, NL, vol. 104, No. 1, Aug. 15, 1995, pp. 81-100.
Markovic A et al, "Gas permeation through porous glass membranes", Journal of Membrane Science, Elsevier Scientific Publ. Company. Amsterdam, NL, vol. 336, No. 1-2, Jul. 1, 2009, pp. 17-31.
The extended European Search Report for European patent application No. 10192016.3 mailing date of Apr. 17, 2012.
Wang X et al., "Investigation on the isotherm of silica gel+water systems: TG and volumetric methods", Journal of Thermal Analysis and Calorimetry, Kluwer Academic Publishers, Dordrecht, NL, vol. 76, No. 2, May 1, 2004, pp. 659-669.

* cited by examiner

Primary Examiner — Frank Lawrence, Jr.
(74) Attorney, Agent, or Firm — Cantor Colburn LLP

(57) ABSTRACT

Information used for creating an adsorption isostere of a substance to be measured in a measuring system (container) is obtained by repeating alternately a first control step of changing temperature or pressure of the measuring system by a fixed amount by adjusting a gas amount supplied to/discharged from the measuring system, and a second control step of changing pressure or temperature of the measuring system by adjusting the gas amount supplied to/discharged from the measuring system until a gas adsorption amount of the substance to be measured becomes the same as before execution of the first control step.

10 Claims, 4 Drawing Sheets

METHOD OF MEASURING INFORMATION FOR ADSORPTION ISOSTERE CREATION, ADSORPTION ISOSTERE CREATION METHOD, ADSORPTION HEAT CALCULATION METHOD, COMPUTER PROGRAM, AND MEASUREMENT SYSTEM

CROSS-REFERENCE TO RELATED APPLICATION

This application is based upon and claims the benefit of priority from Japanese Patent Application No. 2009-266783, filed on Nov. 24, 2009, the disclosure of which is incorporated herein in its entirety by reference.

BACKGROUND OF THE INVENTION

1. Field of the Invention

The present invention relates to a method of measuring information for adsorption isostere creation, an adsorption isostere creation method, an adsorption heat calculation method, a computer program therefor, and a measurement system therefor.

2. Description of Related Art

Up to now, an adsorption capacity of a solid substance, in particular, a porous substance is measured by a heat amount measurement method, a method of measuring an adsorption isotherm or an adsorption isobar, or other such method. Further, the inventor of the present invention proposes a measurement apparatus capable of creating an adsorption isostere based on a measurement result produced when temperature and pressure inside a container are changed while an adsorption amount of the porous substance located inside the container is maintained constant in order to facilitate evaluation of various kinds of characteristics of the porous substance (see Patent Document 1). The measurement apparatus, which includes a weight detection unit for detecting a weight of the porous substance, can perform feedback control for maintaining the adsorption amount of the porous substance constant by controlling a gas amount supplied to the inside of the container or a gas amount discharged to the outside of the container based on a detection weight detected by the weight detection unit.

Meanwhile, among various kinds of adsorption characteristics of the solid substance, an adsorption heat may particularly serve as a physical property value important in an attempt to develop a novel material or apply the material to various kinds of products. In particular, in a case where the solid substance is a porous substance, the adsorption heat is normally a crucially important physical property value that must be grasped. Examples of a method of measuring the adsorption heat include: a method (i) of measuring the adsorption isotherm or the adsorption isobar and calculating the adsorption heat from a Clapeyron-Clausius equation by using the adsorption isostere created based on data obtained from the measurement; and a method (ii) of calculating the adsorption heat from the Clapeyron-Clausius equation by using the adsorption isostere measured by using the above-mentioned measurement apparatus proposed by the inventor of the present invention.

PRIOR ART DOCUMENT

[Patent Document 1] JP 2007-64731 A (Claim 7, Paragraph 0016, etc.),

SUMMARY OF THE INVENTION

However, the adsorption isotherm or the adsorption isobar needs to be measured in the method (i), but in order to create the adsorption isostere, an enormous amount of data needs to be measured. As a result, it takes a long time from a start of measurement until the adsorption heat is determined. Further, in the method (ii), the feedback control needs to be performed based on the detection weight detected by the weight detection unit in order to maintain the adsorption amount of the porous substance constant at a time of measurement. However, an apparatus that can be used as the weight detection unit is expensive. In addition, measurement accuracy thereof is on the order of 1 μg, which leads to low accuracy of data on the adsorption isostere and the adsorption heat that are resultantly determined.

The present invention has been made in view of the above-mentioned circumstances, and an object thereof is to provide a method of measuring information for adsorption isostere creation, in which a time required for determining an adsorption heat and an adsorption isostere can be reduced and the determined adsorption heat and the determined adsorption isostere are high in accuracy, an adsorption isostere creation method and an adsorption heat calculation method that use the method of measuring information for adsorption isostere creation, a computer program for executing the above-mentioned methods, and a measurement system using the above-mentioned methods.

The above-mentioned object is achieved by the present invention as follows. That is, a method of measuring information for adsorption isostere creation according to the present invention includes:

changing pressure and temperature inside a container having a fixed capacity, which is filled with a gas of specific composition and in which a substance to be measured is located, by repeating the following steps alternately at least twice, the following steps including:

(i) a first control step of controlling one of temperature and pressure inside the container for said one of temperature and pressure to be changed by a predetermined variation in a condition of the other of temperature and pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of said one of temperature and pressure; and (ii) a second control step of controlling a gas flow rate for an adsorption amount of the gas of specific composition with respect to the substance to be measured, which has been changed by execution of the first control step, to become the same as an adsorption amount of the gas of specific composition with respect to the substance to be measured, which is obtained before the execution of the first control step, in a condition of said one of temperature and pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the first control step is executed; and obtaining the information for adsorption isostere creation, which is a set of at least three measurement information items each containing a pair of one pressure value and one temperature value, by measuring at least three information items selected from a virtual measurement information group of at least three information items each containing a pair of one pressure value and one temperature value indicated by Expression (1) below.

$$[T(O), P(O)] + \sum_{a=1}^{n} [T(a), P(a)] \qquad (1)$$

In Expression (1), T(0) represents a temperature inside the container, which is measured before first execution of one of the control steps executed in a constant pressure, T(a) represents a temperature inside the container, which is measured at least one time point within a time period between a-th execution and (a+1)-th execution of said one of the control steps, P(0) represents a pressure inside the container, which is measured before first execution of the other of control steps executed in a constant temperature, P(a) represents a pressure inside the container, which is measured at least one time point within a time period between a-th execution and (a+1)-th execution of the other of the control steps, "a" represents an integer equal to or larger than 1, and "n" represents an integer equal to or larger than 2.

Namely, one mode of the method of measuring information for adsorption isostere creation according to the present invention includes;

changing pressure and temperature inside a container having a fixed capacity, which is filled with a gas of specific composition and in which a substance to be measured is located, by repeating the following steps alternately at least twice, the following steps including:
(i) a temperature control step of controlling temperature inside the container for temperature to be changed by a predetermined variation in a condition of pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of temperature; and
(ii) a gas flow rate control step of controlling a gas flow rate for an adsorption amount of the gas of specific composition with respect to the substance to be measured, which has been changed by execution of the temperature control step, to become the same as an adsorption amount of the gas of specific composition with respect to the substance to be measured, which is obtained before the execution of the temperature control step, in a condition of temperature inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the temperature control step is executed; and obtaining the information for adsorption isostere creation, which is a set of at least three measurement information items each containing a pair of one pressure value and one temperature value, by measuring at least three information items selected from a virtual measurement information group of at least three information items each containing a pair of one pressure value and one temperature value indicated by Expression (1') below.

$$[T(O), P(O)] + \sum_{a_1=1}^{n} [T(a_1), P(a_1)] \qquad (1')$$

In Expression (1'), T(0) represents a temperature inside the container, which is measured before first execution of the temperature control step, T($a_1$) represents a temperature inside the container, which is measured at least one time point within a time period between $a_1$-th execution and ($a_1$+1)-th execution of the temperature control step, P(0) represents a pressure inside the container, which is measured before first execution of the gas flow rate control step, P($a_1$) represents a pressure inside the container, which is measured at least one time point within a time period between $a_1$-th execution and ($a_1$+1)-th execution of the gas flow control step, "$a_1$" represents an integer equal to or larger than 1, and "n" represents an integer equal to or larger than 2.

Another mode of the method of measuring information for adsorption isostere creation according to the present invention includes;

changing pressure and temperature inside a container having a fixed capacity, which is filled with a gas of specific composition and in which a substance to be measured is located, by repeating the following steps alternately at least twice, the following steps including:
(i) a pressure control step of controlling pressure inside the container for pressure to be changed by a predetermined variation in condition of temperature inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring temperature inside the container, a result of measuring pressure inside the container, and the variation of pressure; and
(ii) a gas flow rate control step of controlling a gas flow rate for an adsorption amount of the gas of specific composition with respect to the substance to be measured, which has been changed by execution of the pressure control step, to become the same as an adsorption amount of the gas of specific composition with respect to the substance to be measured, which is obtained before the execution of the pressure control step, in a condition of pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the pressure control step is executed; and obtaining the information for adsorption isostere creation, which is a set of at least three measurement information items each containing a pair of one pressure value and one temperature value, by measuring at least three information items selected from a virtual measurement information group of at least three information items each containing a pair of one pressure value and one temperature value indicated by Expression (1″) below.

$$[T(O), P(O)] + \sum_{a_2=1}^{n} [T(a_2), P(a_2)] \quad (1'')$$

In Expression (1″), $T(0)$ represents a temperature inside the container, which is measured before first execution of the gas flow control step pressure, $T(a_2)$ represents a temperature inside the container, which is measured at least one time point within a time period between $a_2$-th execution and $(a_2+1)$-th execution of the gas flow control step, $P(0)$ represents a pressure inside the container, which is measured before first execution of the pressure control step, $P(a_2)$ represents a pressure inside the container, which is measured at least one time point within a time period between $a_2$-th execution and $(a_2+1)$-th execution of the pressure control step, "$a_2$" represents an integer equal to or larger than 1, and "n" represents an integer equal to or larger than 2.

The method of measuring information for adsorption isostere creation according to the a first aspect of the present invention may be carried by a measurement system used for measuring information for adsorption isostere creation, which preferably includes at least: the container; a gas supply channel connected to the container, for supplying the gas of specific composition from the outside of the container to the inside of the container; a gas discharge channel connected to the container, for discharging the gas of specific composition inside the container from the inside of the container to the outside of the container; a gas supply amount control unit provided on the gas supply channel, for controlling the gas supply amount of the gas of specific composition, which is supplied from the outside of the container to the inside of the container; a gas discharge amount control unit provided on the gas discharge channel, for controlling the gas discharge amount of the gas of specific composition, which is discharged from the inside of the container to the outside of the container; a temperature control unit for controlling temperature inside the container; a pressure control unit for controlling pressure inside the container; a gas supply amount measuring unit provided on the gas supply channel, for measuring the gas supply amount; a gas discharge amount measuring unit provided on the gas discharge channel, for measuring the gas discharge amount; a temperature measuring unit for measuring temperature inside the container; a pressure measuring unit for measuring pressure inside the container; and a parameter control unit including a function of controlling at least one kind of parameter value selected from the group consisting of the gas supply amount, the gas discharge amount, temperature, and pressure, based on at least one kind of input value selected from the group consisting of: a measurement value group measured by at least one measuring unit selected from the group consisting of the gas supply amount measuring unit, the gas discharge amount measuring unit, the temperature measuring unit, and the pressure measuring unit; and a setting value group of at least one selected from the group consisting of the gas supply amount, the gas discharge amount, a temperature variation, and a pressure variation that are set in advance; in which the parameter control unit preferably includes at least a function of executing the first control step, that is the temperature control step or the pressure control step, and the second control step, that is the gas flow control step.

In the method of measuring information for adsorption isostere creation according to the present invention, it is preferred that a substance to be measured is a porous substance.

An adsorption isostere creation method according to the present invention includes using the information for adsorption isostere creation obtained by the method of measuring information for adsorption isostere creation according to the present invention, to thereby create an adsorption isostere of the substance to be measured.

An adsorption heat calculation method according to the present invention includes using the information for adsorption isostere creation obtained by the method of measuring information for adsorption isostere creation according to the present invention, to thereby calculate an adsorption heat of the substance to be measured.

A computer program according to the present invention causes a computer to execute at least the following steps, for a step of changing pressure and temperature inside a container having a fixed capacity, which is filled with a gas of specific composition and in which a substance to be measured is located:

(i) a first control step of controlling one of temperature and pressure inside the container for said one of temperature and pressure to be changed by a predetermined variation in a condition of the other of temperature and pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of said one of temperature and pressure; and (ii) a second control step of controlling a gas flow rate for an adsorption amount of the gas of specific composition with respect to the substance to be measured, which has been changed by execution of the first control step, to become the same as an adsorption amount of the gas of specific composition with respect to the substance to be measured, which is obtained before the execution of the first control step, in a condition of said one of temperature and pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the first control step is executed;

and the computer program further causes the computer to execute at least the following step:

(iii) an adsorption isostere creation-purpose information measurement step of, when pressure and temperature inside the container are changed by repeating the first control step and the second control step alternately at least twice, obtaining information for adsorption isostere creation, which is a set of at least three measurement information items each containing a pair of one pressure value and one temperature value, by measuring at least three information items selected from a virtual measurement information group of at least three information items each containing a pair of one pressure value and one temperature value indicated by Expression (1).

The computer program according to the present invention preferably further cause the computer to execute an adsorption isostere creation step of using the information for adsorption isostere creation, to thereby create an adsorption isostere of the substance to be measured.

The computer program according to the present invention preferably further cause the computer to execute an adsorption heat calculation step of using the information for adsorption isostere creation, to thereby calculate an adsorption heat of the substance to be measured.

A measurement system according to the present invention includes at least: a container; a gas supply channel connected to the container, for supplying a gas of specific composition from the outside of the container to the inside of the container; a gas discharge channel connected to the container, for discharging the gas of specific composition inside the container from the inside of the container to the outside of the container; a gas supply amount control unit provided on the gas supply channel, for controlling a gas supply amount of the gas of specific composition, which is supplied from the outside of the container to the inside of the container; a gas discharge amount control unit provided on the gas discharge channel, for controlling a gas discharge amount of the gas of specific composition, which is discharged from the inside of the container to the outside of the container; a temperature control unit for controlling temperature inside the container; a pressure control unit for controlling pressure inside the container; a gas supply amount measuring unit provided on the gas supply channel, for measuring the gas supply amount; a gas discharge amount measuring unit provided on the gas discharge channel, for measuring the gas discharge amount; a temperature measuring unit for measuring temperature inside the container; a pressure measuring unit for measuring pressure inside the container; a parameter control unit including a function of controlling at least one kind of parameter value selected from the group consisting of the gas supply amount, the gas discharge amount, temperature, and pressure, based on at least one kind of input value selected from the group consisting of: a measurement value group measured by at least one measuring unit selected from the group consisting of the gas supply amount measuring unit, the gas discharge amount measuring unit, the temperature measuring unit, and the pressure measuring unit; and a setting value group of at least one selected from the group consisting of the gas supply amount, the gas discharge amount, a temperature variation, and a pressure variation that are set in advance; and a recording unit for recording at least one kind of measurement value selected from the measurement value group, in which:

the parameter control unit includes at least a function of repeating the following steps alternately at least twice, the following steps including:

(i) a first control step of controlling one of temperature and pressure inside the container for said one of temperature and pressure to be changed by a predetermined variation in a condition of the other of temperature and pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of said one of temperature and pressure; and (ii) a second control step of controlling a gas flow rate for an adsorption amount of the gas of specific composition with respect to the substance to be measured, which has been changed by execution of the first control step, to become the same as an adsorption amount of the gas of specific composition with respect to the substance to be measured, which is obtained before the execution of the first control step, in a condition of said one of temperature and pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the first control step is executed; and the recording unit includes at least a function of, in a process from before the first control step being executed to the first control step and the second control step being alternately executed, recording information for adsorption isostere creation, which is a set of at least three measurement information items each containing a pair of one pressure value and one temperature value and which is obtained by measuring at least three information items selected from a virtual measurement information group of at least three information items each containing a pair of one pressure value and one temperature value indicated by Expression (1).

The present invention is possible to provide a method of measuring information for adsorption isostere creation in which a time required for determining the adsorption heat and the adsorption isostere can be reduced and the determined adsorption heat and the determined adsorption isostere are high in accuracy. The present invention is also possible to provide an adsorption isostere creation method and an adsorption heat calculation method that use the method of measuring information for adsorption isostere creation. The present invention is further possible to provide a computer program for executing the above-mentioned method, and a measurement system using the above-mentioned method.

BRIEF DESCRIPTION OF THE DRAWINGS

Specific embodiments of the present invention will now be described, by way of example only, with reference to the accompanying drawings in which.

DETAILED DESCRIPTION OF THE PREFERRED EMBODIMENTS

Figure 1A:
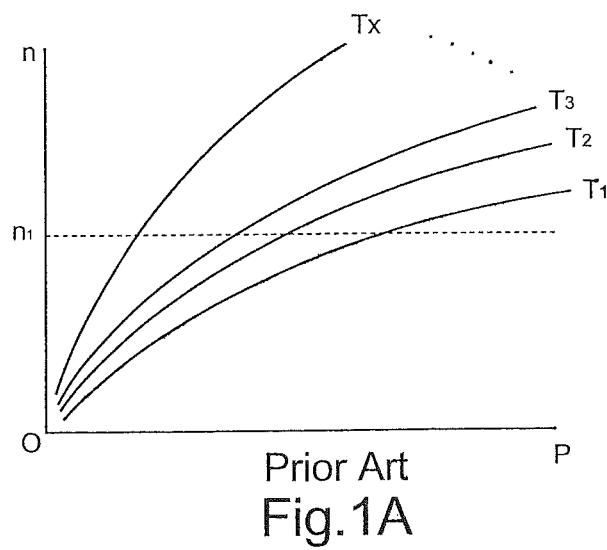
FIG. 1A to FIG. 1C are schematic diagrams illustrating an example of a conventional creation method for an adsorption isostere.

Method of Measuring Information for Adsorption Isostere Creation

In a method of measuring information for adsorption isostere creation according to a first embodiment: pressure and temperature inside a container having a fixed capacity, which is filled with a gas of specific composition and in which a substance to be measured is located, are changed by repeating alternately at least twice a (A) temperature control step described below and a (B) gas flow rate control step described below; and the information for adsorption isostere creation, which is a set of at least three measurement information items each containing a pair of one pressure value and one temperature value, is obtained by measuring at least three information items selected from a virtual measurement information group of at least three information items each containing a pair of one pressure value and one temperature value indicated by Expression (1') below.

(A) Temperature Control Step

In the temperature control step, temperature inside the container is controlled by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and a predetermined temperature variation, so that temperature inside the container is changed by the predetermined temperature variation while pressure inside the container is maintained constant.

(B) Gas Flow Rate Control Step

In the gas flow rate control step, a gas flow rate is controlled by performing the feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the temperature control step is executed, so that an adsorption amount of the gas of specific composition with respect to the substance to be measured, which has been changed by execution of the temperature control step, becomes the same as an adsorption amount of the gas of specific composition with respect to the substance to be measured, which is obtained before the execution of the temperature control step, while temperature inside the container is maintained constant.

$$[T(O), P(O)] + \sum_{a_1=1}^{n} [T(a_1), P(a_1)] \quad (1')$$

In Expression (1'), $T(0)$ represents temperature inside the container, which is measured before first execution of the temperature control step, $T(a_1)$ represents temperature inside the container, which is measured at least one time point within a time period between $a_1$-th execution and $(a_1+1)$-th execution of the temperature control step, $P(0)$ represents pressure inside the container, which is measured before first execution of the gas flow rate control step, $P(a_1)$ represents pressure inside the container, which is measured at least one time point within a time period between $a_1$-th execution and $(a_1+1)$-th execution of the gas flow rate control step, "$a_1$" represents an integer equal to or larger than 1, and "n" represents an integer equal to or larger than 2.

In the method of measuring information for adsorption isostere creation according to the first embodiment, in the above-mentioned process of repeating the temperature control step and the gas flow rate control step, it is possible to obtain a minimum amount of measurement data necessary to create an adsorption isostere by measuring the at least three information items selected from the virtual measurement information group indicated by Expression (1'). As a result, immediately after that, the adsorption isostere and an adsorption heat amount can be obtained by performing information processing by using a computer based on the obtained measurement data. Therefore, it is not necessary to measure an enormous amount of data because the adsorption heat and the adsorption isostere are determined in comparison with a method of creating the adsorption isostere based on the measurement data obtained by measuring a plurality of adsorption isotherms or a plurality of adsorption isobars or a method of calculating an adsorption heat from a Clapeyron-Clausius equation. Accordingly, it is possible to greatly reduce a time required for creating the adsorption isostere and a time required for obtaining a result of calculating the adsorption heat.

Figure 1B:
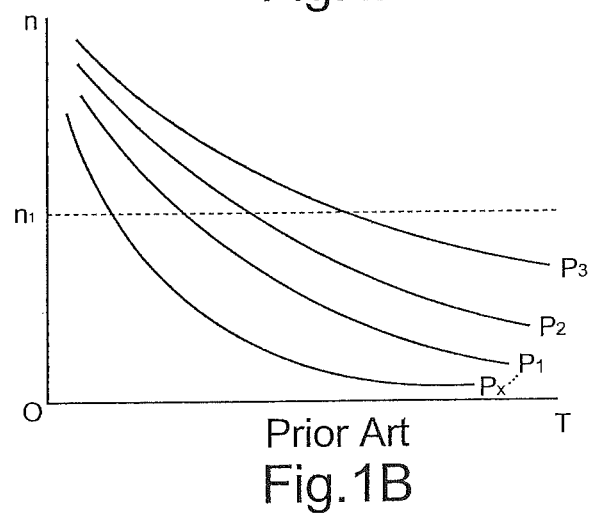
Figure 1C:
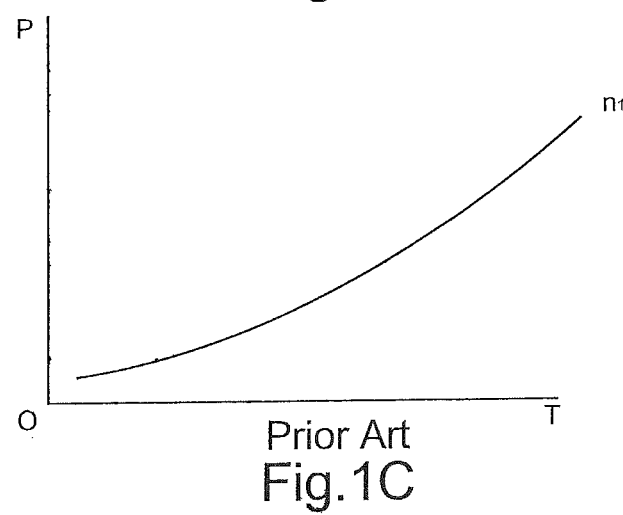

The above-mentioned effect is described below in more detail with reference to the drawings. FIG. 1A to FIG. 1C are schematic diagrams illustrating an example of a conventional creation method for an adsorption isostere, in which FIG. 1A indicates adsorption isotherms, FIG. 1B indicates adsorption isobars, and FIG. 1C indicates an adsorption isostere. In FIG. 1A, the horizontal axis represents pressure P, and the vertical axis represents an adsorption amount n. In FIG. 1B, the horizontal axis represents temperature T, and the vertical axis represents the adsorption amount n. In FIG. 1C, the horizontal axis represents temperature T, and the vertical axis represents pressure P. Temperature T and pressure P mean temperature and pressure inside a measuring system in which the substance to be measured is located, respectively, and the adsorption amount n means an amount of gas adsorbed to the substance to be measured. Further, in FIG. 1A, a plurality of lines indicated by symbols $T_1$ to $T_x$ mean the adsorption isotherms under a temperature $T_1$ to a temperature $T_x$, respectively. In FIG. 1B, a plurality of lines indicated by symbols $P_1$ to $P_X$ mean the adsorption isobars under a pressure $P_1$ to a pressure $P_x$, respectively. In FIG. 1C, one line indicated by symbol $n_1$ means the adsorption isostere with an adsorption amount $n_1$.

Here, as illustrated in FIG. 1C, the adsorption isostere is expressed as a graph representing a relationship between temperature T and pressure P in a case where a gas adsorption amount with respect to the substance to be measured and subjected to gas adsorption/degassing reaction is fixed. Therefore, data on temperature T and pressure P measured in a state in which the gas adsorption amount with respect to the substance to be measured is fixed to "$n_1$" is necessary for creation of the adsorption isostere.

In contrast, the adsorption isotherms illustrated in FIG. 1A are expressed as graphs representing relationships between the gas adsorption amount n and pressure P in a case where temperature is fixed inside the measuring system in which the substance to be measured and subjected to the gas adsorption/degassing reaction is located. The adsorption isobars illustrated in FIG. 1B are expressed as graphs representing relationships between the gas adsorption amount n and temperature T in a case where pressure is fixed inside the measuring system in which the substance to be measured and subjected to the gas adsorption/degassing reaction is located.

Therefore, if data for the creation of the adsorption isostere illustrated in FIG. 1C, that is, information containing temperature T and pressure P in the case where the adsorption amount n is fixed to "$n_1$", is to be obtained based on the adsorption isotherms illustrated in FIG. 1A, it is necessary to measure a plurality of adsorption isotherms, each of which intersects a line of the adsorption amount n being $n_1$ (dotted line of FIG. 1A), in various temperature T. That is, as illustrated in FIG. 1A, a plurality of adsorption isotherms of from an adsorption isotherm at a temperature $T_1$ to an adsorption isotherm at a temperature Tx are necessary. In addition, to secure the accuracy of the adsorption isostere to be created, as many adsorption isotherms as possible need to be measured. This holds true in a case where data for the creation of the adsorption isostere illustrated in FIG. 1C is to be obtained based on the plurality of adsorption isobars illustrated in FIG. 1B.

Figure 2:
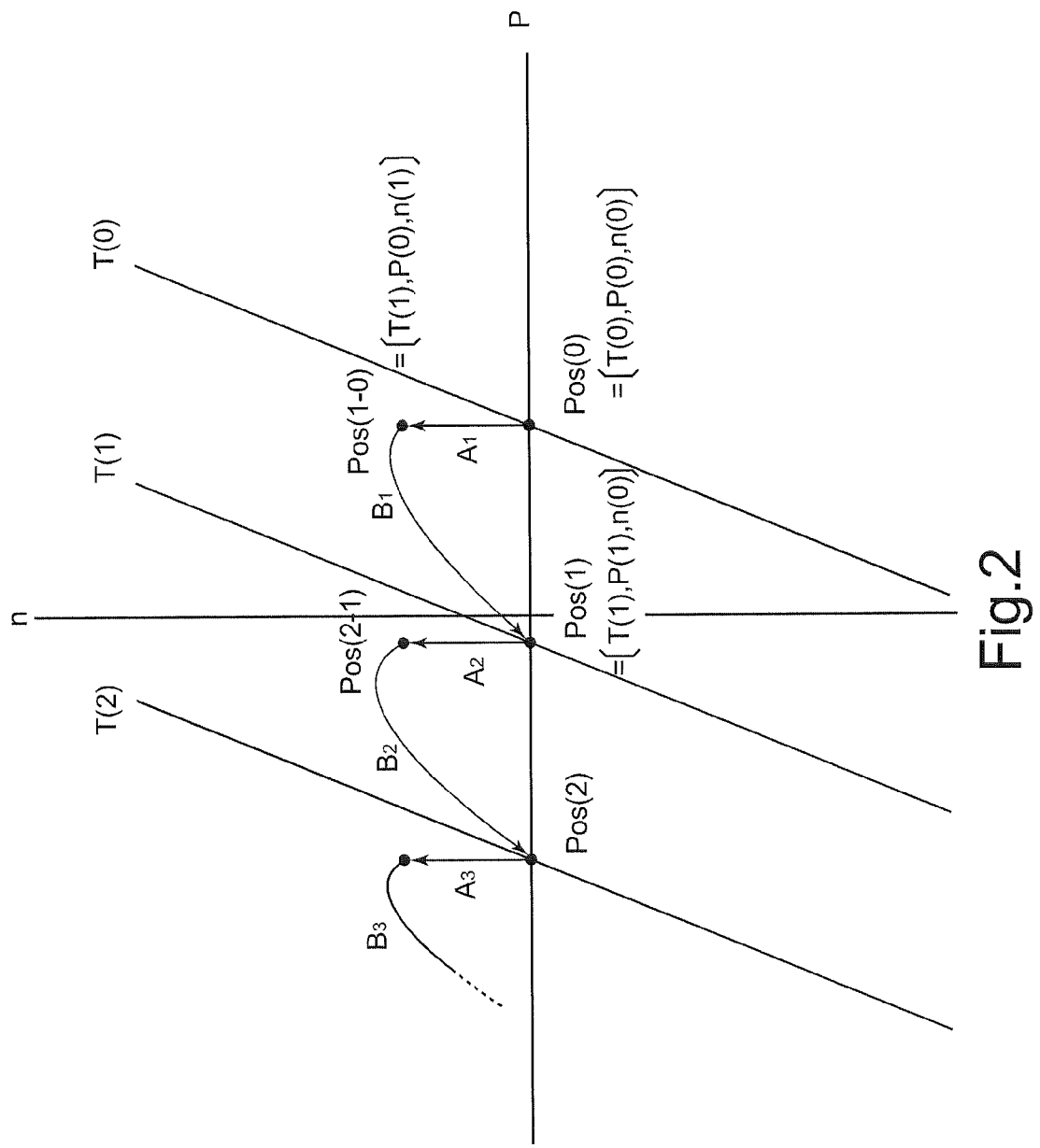
FIG. 2 is an explanatory diagram illustrating a method of measuring information for adsorption isostere creation according to a first embodiment of the present invention.

The method of measuring information for adsorption isostere creation according to the first embodiment is described in more detail with reference to the drawings. FIG. 2 is an explanatory diagram illustrating an example of the method of measuring information for adsorption isostere creation according to the first embodiment, in which the horizontal axis represents pressure P, and the vertical axis represents the adsorption amount n of the gas of specific composition with respect to the substance to be measured. In FIG. 2, the origin point means a point having an arbitrary pressure P and an arbitrary adsorption amount n instead of meaning a point representing zero for both pressure P and the adsorption amount n. Further, in FIG. 2, a line indicated by symbol T(0) means an adsorption isotherm at a temperature T(0), a line indicated by symbol T(1) means an adsorption isotherm at a temperature T(1), and a line indicated by symbol T(2) means an adsorption isotherm at a temperature T(2). Further, the temperatures T(0), T(1), and T(2) satisfy a relationship of T(2)<T(1)<T(0).

First, after the substance to be measured is located inside the container having a capacity V, the inside of the container is replaced with the gas of specific composition (hereinafter, may be referred to simply as "gas"), and the process stands by until the gas adsorption/degassing reaction with respect to the substance to be measured achieves a state of equilibrium. Then, the initial temperature, the initial pressure, and the initial adsorption amount in this state are set as P(0), T(0), and n(0), respectively, and are indicated by a position $P_{OS}(0)$ in FIG. 2. Subsequently, in the process of executing the temperature control step and the gas flow rate control step alternately in the stated order, starting from the above-mentioned state, all temperature values and pressure values indicated as the virtual measurement information group by Expression (1), to thereby obtain the information for adsorption isostere creation.

The relationship among temperature T, pressure P, and the adsorption amount n inside the measuring system are described before the details of the temperature control step and the gas flow rate control step are described. Here, in the container (measuring system) having a fixed capacity, which is filled with the gas and in which the substance to be measured is located, a relationship expressed by Expression (2) below is established among temperature T, pressure P, and the adsorption amount n. The container can have the gas supplied from the outside to the inside of the container as necessary and discharge the gas from the container to the outside.

$$\Delta n = \Delta n_i - \frac{V}{RT}\Delta P \qquad (2)$$

In Expression (2), $\Delta n$ represents a change (mol) of the adsorption amount of the gas with respect to the substance to be measured, $\Delta n_i$ represents an amount (mol) of gas supplied to the inside of the container or discharged to the outside of the container, $\Delta p$ represents a change (Torr) in pressure inside the container, V represents a capacity ($cm^3$) of the container, R represents a gas constant, that is, 0.0624 $cm^3$-Torr/K·mol, and T represents temperature (K) inside the container. Hereinafter, the temperature control step and the gas flow rate control step are described in detail.

First, in the initial state $P_{OS}(0)$, first execution of the temperature control step, hereinafter referred as a "first temperature control step A1", is carried. In this case, temperature T is reduced from T(0) by a predetermined temperature variation while pressure P is maintained at P(0). Here, the gas adsorption amount n of the substance to be measured increases if temperature T is to be reduced by the predetermined temperature variation, and hence the gas needs to be supplied to the inside of the container in order to maintain pressure P at P(0). A gas supply amount of the gas supplied to the inside of the container is subjected to feedback control based on a result of measuring pressure P inside the container, a result of measuring temperature T inside the container, and a predetermined temperature variation [T(1)−T(0)] during the execution of the first temperature control step A1. That is, the temperature T(0) and the temperature variation [T(1)−T(0)] are known before the execution of the first temperature control step A1, and hence a target temperature T(1) to be a target of the control is calculated based on the above-mentioned information. Then, during the execution of the first temperature control step A1, control of the gas supply amount and control of whether or not to end the first temperature control step A1 are performed based on a result of successively measuring pressure P inside the container and judging whether or not pressure P is maintained constant and a result of successively measuring temperature T inside the container and judging whether or not the measurement result is approaching, or exactly matches, the target temperature T(1).

This allows temperature T to change from T(0) to T(1) without fail while pressure P is maintained at P(0). Then, when the execution of the first temperature control step A1 is ended, temperature T, pressure P, and the adsorption amount n become $T(1)$, $P(0)$, and $n(1)$, respectively, and are indicated by a position $P_{OS}(1\text{-}0)$ in FIG. 2.

Next, first execution of the gas flow rate control step, hereinafter referred as a "first gas flow rate control step B1", is carried in $P_{OS}(1\text{-}0)$. In this case, the adsorption amount n is reduced from $n(1)$ to the initial value $n(0)$ while temperature T is maintained at $T(1)$. Here, if the adsorption amount n is to be reduced from $n(1)$ to $n(0)$ while temperature T inside the container is maintained at $T(1)$, pressure P inside the container needs to be reduced. Then, if pressure P inside the container is to be reduced, the gas needs to be discharged to the outside of the container. A gas discharge amount of the gas to be discharged to the outside of the container is subjected to feedback control based on <a> a result of measuring the gas supply amount of the gas supplied to the inside of the container during the execution of the first gas flow rate control step B1 and <b> a result of measuring a variation $[n(1)\text{-}n(0)]$ of the gas adsorption amount of the substance to be measured between before and after the execution of the first temperature control step A1, in other words, a total amount of a gas newly supplied to the inside of the container during the execution of the first temperature control step A1.

That is, the variation $[n(1)\text{-}n(0)]$ of the gas adsorption amount of the substance to be measured is known before the execution of the first gas flow rate control step B1, and hence, during the execution of the first gas flow rate control step B1, control of the gas discharge amount and control of whether or not to end the gas flow rate control step B1 are performed based on a result of successively measuring the gas flow rate per unit time of the gas discharged from the inside of the container, obtaining a cumulative gas flow rate, and judging whether or not the cumulative gas flow rate is approaching, or exactly matches, the variation $[n(1)\text{-}n(0)]$.

This allows the gas adsorption amount with respect to the substance to be measured to be reduced from $n(1)$ to the initial value $n(0)$ without fail while temperature T is maintained at $T(1)$. Further, when the execution of the above-mentioned process is ended, pressure P inside the container is accordingly reduced from $P(0)$ to $P(1)$. That is, when the execution of the first gas flow rate control step B1 is ended, temperature T, pressure P, and the adsorption amount n become $T(1)$, $P(1)$, and $n(0)$, respectively, and are indicated by a position $P_{OS}(1)$ in FIG. 2.

Two information items of $[T(0), P(0)]$ and $[T(1), P(1)]$ are thus obtained as information items containing a pair of (temperature T, pressure P) with the gas adsorption amount $n(0)$ when the first temperature control step A1 and the first gas flow rate control step B1 are ended. If a second temperature control step A2 and a second gas flow rate control step B2 are executed in the same manner, an information item $[T(2), P(2)]$ can be further obtained as an information item containing a pair of (temperature T, pressure P) with the gas adsorption amount $n(0)$.

In the example illustrated in FIG. 2, assuming that x is set as an integer equal to or larger than 0, the process of one temperature control step and one pressure control step is executed only once between the measurement of temperature T and pressure P in $P_{OS}(x)$ and the measurement of temperature T and pressure P in $P_{OS}(x+1)$. However, temperature T and pressure P are not necessarily measured every time the above-mentioned process is repeated, and may be measured after the process is repeated several times. For example, in the example illustrated in FIG. 2, temperature T and pressure P are measured in respective positions with a value of x incremented by one, that is, in $P_{OS}(0)$, $P_{OS}(1)$, $P_{OS}(2)$, $P_{OS}(3)$ . . . , and the obtained values are set as the information for adsorption isostere creation, but temperature T and pressure P may be measured only in positions with the value of x incremented by five, that is, in $P_{OS}(0)$, $P_{OS}(5)$, $P_{OS}(10)$, $P_{OS}(15)$ . . . , and the obtained values may be set as the information for adsorption isostere creation.

In the case illustrated in FIG. 2, temperature T is reduced to increase the adsorption amount n in the temperature control step, and in the gas flow rate control step, the gas flow rate is controlled to thereby reduce the adsorption amount n to the initial value with the result that pressure P is accordingly reduced. However, the temperature control step and the gas flow rate control step may be executed in a manner opposite to the case illustrated in FIG. 2. In this case, temperature T is increased to reduce the adsorption amount n in the temperature control step, and in the gas flow rate control step, the gas flow rate is controlled to thereby increase the adsorption amount n to the initial value with the result that pressure P is accordingly increased. Therefore, also in this case, it is possible to obtain the information for adsorption isostere creation.

The temperature control step and the gas flow rate control step need to be repeated alternately at least twice. By setting the number of times the temperature control step and the gas flow rate control step are repeated alternately to at least two, it is possible to obtain such information for adsorption isostere creation that is a set of three information items or more (temperature T, pressure P) necessary for the creation of the adsorption isostere. It is preferred that the number of times the temperature control step and the gas flow rate control step are repeated alternately be set to at least three, and more preferably, at least five, from the viewpoint of further improving the accuracy of the adsorption isostere and the adsorption heat obtained based on the information for adsorption isostere creation. Further, there is no particular limitation on an upper limit of the number of times the temperature control step and the gas flow rate control step are repeated alternately, but it is preferred that the upper limit be set to 100 times or smaller in terms of practicality from a balance between a time required for determining the adsorption isostere and the adsorption heat and effects of improving the accuracy of the adsorption isostere and the adsorption heat determined based on the information for adsorption isostere creation.

In order to obtain the adsorption isostere and the adsorption heat that are high in accuracy, it is important that the measurement accuracy of temperature and pressure that are measured after being selected from the virtual measurement information group indicated by Expression (1') is high. There are various kinds of factors that affect the measurement accuracy of temperature and pressure. However, the method of measuring information for adsorption isostere creation according to the first embodiment is greatly different from the method disclosed in Patent Document 1 in the following point. That is, in contrast to the method of measuring the adsorption isostere by using a measurement system for performing the feedback control based on the result of detecting by a weight detection unit a change in weight involved in the gas adsorption and the degassing reaction for a porous substance being the substance to be measured, in the method of measuring information for adsorption isostere creation according to the first embodiment, the change in weight involved in the gas adsorption and the degassing reaction for the substance to be measured is indirectly grasped by measuring the gas flow rate of the gas supplied to the inside of or discharged to the outside of the container in which the substance to be measured is located. Then, based on a result thereof, the feedback control is performed.

In summary, to obtain the measurement data necessary for the creation of the adsorption isostere, in Patent Document 1, the change in weight of the substance to be measured is directly detected by the weight measurement apparatus to perform the feedback control (weight-basis feedback control) thereon, while in the method of measuring information for adsorption isostere creation according to the first embodiment, the change in weight is indirectly detected by measuring the gas flow rate to perform the feedback control (gas flow rate-basis feedback control) thereon. In addition, the weight-basis feedback control is performed based on a weight measurement having measurement accuracy on the order of 1 µg, while the gas flow rate-basis feedback control is performed based on the gas flow rate measurement having measurement accuracy on the order of 0.01 µg in terms of weight basis. Therefore, the method of measuring information for adsorption isostere creation according to the first embodiment which employs the gas flow rate-basis feedback control allows more precise feedback control to be performed than the method disclosed in Patent Document 1, and hence the accuracy of the measurement data necessary for the creation of the adsorption isostere is higher with the result that the accuracy of the adsorption heat and the adsorption isostere determined based on the measurement data is also higher.

For reference sake, a quartz spring or a magnetic levitation scale is normally used as such a weight measurement apparatus used for the weight-basis feedback control because of high universality that allows use for a corrosive gas and maintainability. Here, the measurement accuracy of the quartz spring is on the order of approximately 2 to 5 µg (see "Colloid Science IV. Experimental Method in Colloid Science", The Chemical Society of Japan ed., Tokyo Kagaku Dojin, p. 187), and the measurement accuracy of the magnetic levitation scale is on the order of approximately 1 µg (see website of Rubotherm GmbH).

On the other hand, a mass flowmeter (mass flow controller) is used as a gas flow rate measurement apparatus used for the gas flow rate-basis feedback control. Here, SEC-Z512KX (full-scale flow rate: ½ sccm, flow rate accuracy: +1.0% of full-scale flow rate) manufactured by HORIBA STEC, Co., Ltd. is used as the mass flowmeter, the measurement accuracy of a time for flowing a gas is set to 1 second, and the measurement accuracy of a case of flowing a hydrogen gas is expressed as "{(full-scale flow rate×flow rate accuracy)/volume of 1 mol of gas in a normal state}×molecular weight of the hydrogen gas×measurement accuracy of the time for flowing the gas". In this expression, the volume of gas in the normal state is 22,414 cm$^3$/mol, and the molecular weight of the hydrogen gas is 2 g/mol. Therefore, the measurement accuracy is found as approximately 0.005 µg from the above-mentioned expression. That is, it is clear that the measurement accuracy obtained by using the mass flowmeter is approximately 100 times as high as the measurement accuracy obtained by using the quartz spring or the magnetic levitation scale.

In addition, in the weight-basis feedback control, in order to correctly perform the weight measurement for the substance to be measured, a heat source or a cooling source cannot be brought into direct contact with the substance to be measured. Therefore, it takes time to control temperature of the substance to be measured to become a predetermined temperature with the result that a measurement time becomes long. Meanwhile, in the gas flow rate-basis feedback control, it is not necessary to perform the weight measurement for the substance to be measured by using the weight measurement apparatus, and it is possible to bring the heat source or the cooling source into direct contact with the substance to be measured. Therefore, it is possible to control temperature of the substance to be measured to quickly become the predetermined temperature with the result that a measurement time can be further reduced. Further, if the heat source or the cooling source is brought into direct contact with the substance to be measured, the measurement becomes possible with a wider temperature range. In particular, there is also such an advantage that the measurement at temperature lower than room temperature becomes easier.

A method of measuring information for adsorption isostere creation according to a second embodiment is described below. In a method of measuring information for adsorption isostere creation according to a second embodiment: pressure and temperature inside a container having a fixed capacity, which is filled with a gas of specific composition and in which a substance to be measured is located, are changed by repeating alternately at least twice a (C) pressure control step described below and a (D) gas flow rate control step described below; and the information for adsorption isostere creation, which is a set of at least three measurement information items each containing a pair of one pressure value and one temperature value, is obtained by measuring at least three information items selected from a virtual measurement information group of at least three information items each containing a pair of one pressure value and one temperature value indicated by Expression (1″) below.

(C) Pressure Control Step

In the pressure control step, pressure inside the container is controlled by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring temperature inside the container, a result of measuring pressure inside the container, and a predetermined pressure variation, so that pressure inside the container is changed by the predetermined pressure variation while temperature inside the container is maintained constant.

(D) Gas Flow Rate Control Step

In the gas flow rate control step, a gas flow rate is controlled by performing the feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the pressure control step is executed, so that an adsorption amount of the gas of specific composition with respect to the substance to be measured, which has been changed by execution of the pressure control step, becomes the same as an adsorption amount of the gas of specific composition with respect to the substance to be measured, which is obtained before the execution of the pressure control step, while pressure inside the container is maintained constant.

$$[T(O), P(O)] + \sum_{a_2=1}^{n} [T(a_2), P(a_2)] \tag{1″}$$

In Expression (1″), T(0) represents a temperature inside the container, which is measured before first execution of the gas flow rate control step, T($a_2$) represents a temperature inside the container, which is measured at least one time point within a time period between $a_2$-th execution and ($a_2$+1)-th execution of the gas flow rate control step, P(0) represents a pressure inside the container, which is measured before first execution of the pressure control step, P(b) represents a pressure inside the container, which is measured at least one time point within a time period between $a_2$-th execution and ($a_2$+1)-th execution of the pressure control step, "$a_2$" represents an integer equal to or larger than 1, and "n" represents an integer equal to or larger than 2.

In the method of measuring information for adsorption isostere creation according to the second embodiment, in the above-mentioned process of repeating the temperature control step and the gas flow rate control step, it is possible to obtain a minimum amount of measurement data necessary to create an adsorption isostere by measuring the at least three information items selected from the virtual measurement information group indicated by Expression (1″). Therefore, in the same manner as in the method of measuring information for adsorption isostere creation according to the first embodiment, it is possible to greatly reduce a time required for determining the adsorption heat and the adsorption isostere compared with the method of creating the adsorption isostere based on the measurement data obtained by measuring adsorption isotherms or adsorption isobars or the method of calculating the adsorption heat from the Clapeyron-Clausius equation.

Figure 3:
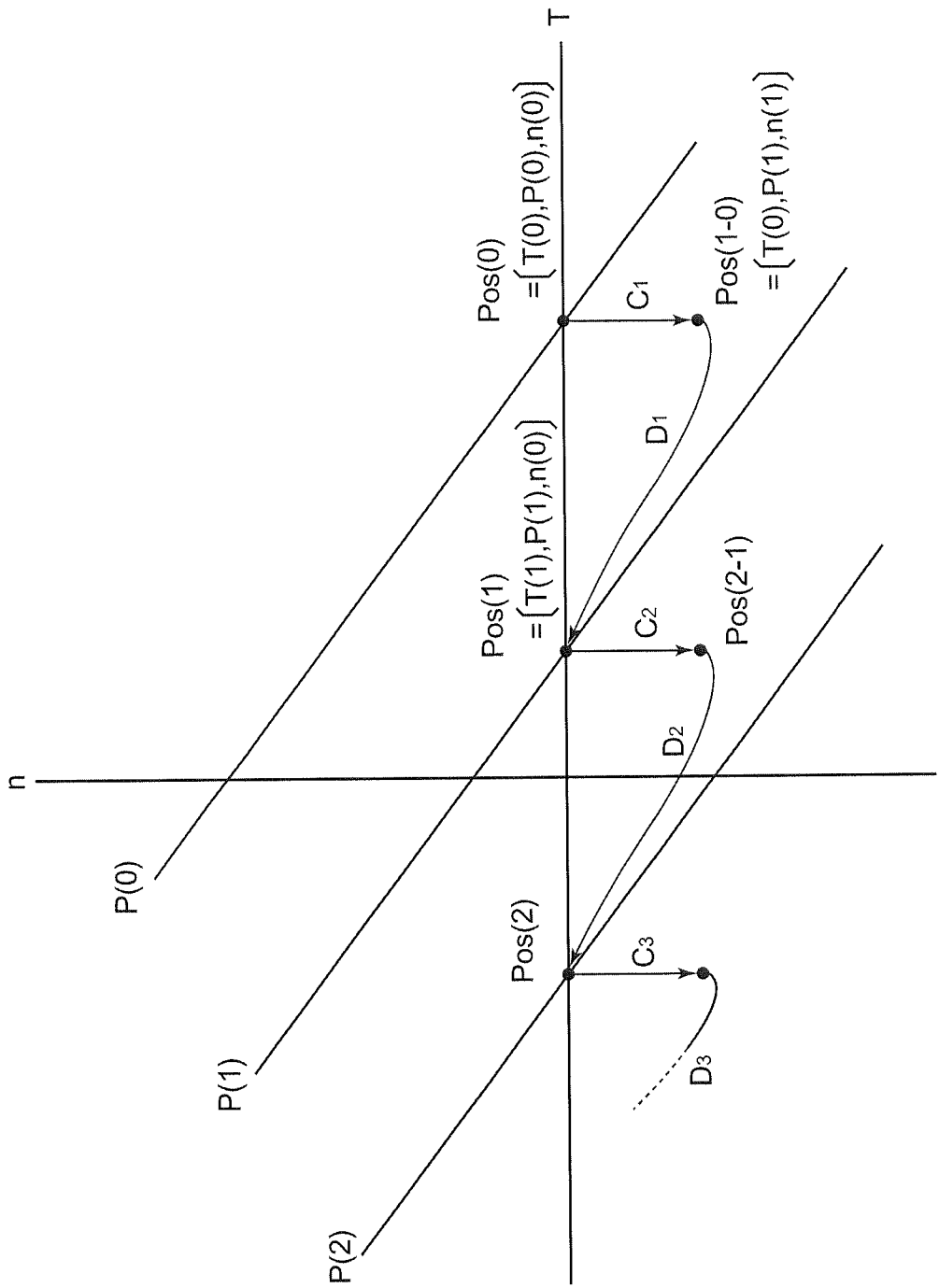
FIG. 3 is an explanatory diagram illustrating a method of measuring information for adsorption isostere creation according to a second embodiment of the present invention.

The method of measuring information for adsorption isostere creation according to the second embodiment is described in more detail with reference to the drawings. FIG. 3 is an explanatory diagram illustrating an example of the method of measuring information for adsorption isostere creation according to the second embodiment, in which the horizontal axis represents temperature T, and the vertical axis represents the adsorption amount n of the gas of specific composition with respect to the substance to be measured. In FIG. 3, the origin point means a point having an arbitrary temperature T and an arbitrary adsorption amount n instead of meaning a point representing zero for both temperature T and the adsorption amount n. Further, in FIG. 3, a line indicated by symbol P(0) means an adsorption isotherm at a pressure P(0), a line indicated by symbol P(1) means an adsorption isotherm at a pressure P(1), and a line indicated by symbol P(2) means an adsorption isotherm at a pressure P(2). Further, the pressures P(0), P(1), and P(2) satisfy a relationship of P(2)<P(1)<P(0).

First, after the substance to be measured is located inside the container having the capacity V, the inside of the container is replaced with the gas, and the process stands by until the gas adsorption/degassing reaction with respect to the substance to be measured achieves a state of equilibrium. Then, the initial temperature, the initial pressure, and the initial adsorption amount in this state are set as P(0), T(0), and n(0), respectively, and are indicated by the position Pos(0) in FIG. 3. Subsequently, in the process of executing the pressure control step and the gas flow rate control step alternately in the stated order, starting from the above-mentioned state, all the temperature values and the pressure values indicated as the virtual measurement information group by Expression (1″) are measured to thereby obtain the information for adsorption isostere creation. The relationship among temperature T, pressure P, and the adsorption amount n inside the container (measuring system) is as expressed by Expression (2) described above. Hereinafter, the temperature control step and the gas flow rate control step are described in detail.

First, in the initial state Pos(0), a first pressure control step C1 is executed. In this case, pressure P is reduced from P(0) by a predetermined temperature variation while temperature T is maintained at T(0). Here, the gas adsorption amount n of the substance to be measured reduces if pressure P is to be reduced by the predetermined pressure variation, and hence the gas needs to be discharged to the outside of the container in order to maintain temperature T at T(0). A gas supply amount of the gas discharged to the outside of the container is subjected to feedback control based on a result of measuring temperature T inside the container, a result of measuring pressure P inside the container, and a predetermined pressure variation [P(1)-P(0)] during the execution of the pressure control step C1. That is, the pressure P(0) and the pressure variation [P(1)-P(0)] are known before the execution of the pressure control step C1, and hence a target pressure P(1) to be a target of the control is calculated based on the above-mentioned information. Then, during the execution of the pressure control step C1, control of the gas supply amount and control of whether or not to end the pressure control step C1 are performed based on a result of successively measuring temperature T inside the container and judging whether or not temperature T is maintained constant and a result of successively measuring pressure P inside the container and judging whether or not the measurement result is approaching, or exactly matches, the target pressure P(1).

This allows pressure P to change from P(0) to P(1) without fail while temperature T is maintained at T(0). Then, when the execution of the first pressure control step C1 is ended, temperature T, pressure P, and the adsorption amount n become T(0), P(1), and n(1), respectively, and are indicated by a position $P_{OS}$(1-0) in FIG. 3.

Next, a first gas flow rate control step D1 is executed in $P_{OS}$(1-0). In this case, the adsorption amount n is increased from n(1) to the initial value n(0) while pressure P is maintained at P(1). Here, if the adsorption amount n is to be increased from n(1) to n(0) while pressure P inside the container is maintained at P(1), temperature T inside the container needs to be reduced. Then, if temperature T inside the container is to be reduced, the gas needs to be supplied to the inside of the container. A gas supply amount of the gas to be supplied to the inside of the container is subjected to feedback control based on <a> a result of measuring the gas discharge amount of the gas discharged to the outside of the container during the execution of the first flow rate control step D1 and <b> a result of measuring a variation [n(1)-n(0)] of the gas adsorption amount of the substance to be measured between before and after the execution of the first pressure control step C1, in other words, a total amount of a gas newly discharged to the outside of the container during the execution of the first pressure control step C1.

That is, the variation [n(1)-n(0)] of the gas adsorption amount of the substance to be measured is known before the execution of the first gas flow rate control step D1, and hence, during the execution of the first gas flow rate control step D1, control of the gas supply amount and control of whether or not to end the gas flow rate control step D1 are performed based on a result of successively measuring the gas flow rate per unit time of the gas supplied to the inside of the container, obtaining a cumulative gas flow rate, and judging whether or not the cumulative gas flow rate is approaching, or exactly matches, the variation [n(1)-n(0)].

This allows the gas adsorption amount with respect to the substance to be measured to be increased from n(1) to the initial value n(0) without fail while pressure P is maintained at P(1). Further, when the execution of the above-mentioned process is ended, temperature T inside the container is accordingly reduced from T(0) to T(1). That is, when the execution of the first gas flow rate control step D1 is ended, temperature T, pressure P, and the adsorption amount n become T(1), P(1), and n(0), respectively, and are indicated by a position Pos(1) in FIG. 3.

Two information items of [T(0), P(0)] and [T(1), P(1)] are thus obtained as information items containing a pair of (temperature T, pressure P) with the gas adsorption amount n(0) when the first pressure control step C1 and the first gas flow rate control step D1 are ended. If a second pressure control step C2 and a second gas flow rate control step D2 are executed in the same manner, an information item [T(2), P(2)] can be further obtained as an information item containing a pair of (temperature T, pressure P) with the gas adsorption amount n(0).

In the example illustrated in FIG. 3, assuming that x is set as an integer equal to or larger than 0, the process of one temperature control step and one pressure control step is executed only once between the measurement of temperature T and pressure P in $P_{OS}(x)$ and the measurement of temperature T and pressure P in $P_{OS}(x+1)$. However, temperature T and pressure P are not necessarily measured every time the above-mentioned process is repeated, and may be measured after the process is repeated several times. For example, in the example illustrated in FIG. 3, temperature T and pressure P are measured in respective positions with a value of x incremented by one, that is, in $P_{OS}(0)$, $P_{OS}(1)$, $P_{OS}(2)$, $P_{OS}(3)$ . . . , and the obtained values are set as the information for adsorption isostere creation, but temperature T and pressure P may be measured only in positions with the value of x incremented by five, that is, in $P_{OS}(0)$, $P_{OS}(5)$, $P_{OS}(10)$, $P_{OS}(15)$ . . . , and the obtained values may be set as the information for adsorption isostere creation.

In the case illustrated in FIG. 3, pressure P is reduced to reduce the adsorption amount n in the pressure control step, and in the gas flow rate control step, the gas flow rate is controlled to thereby increase the adsorption amount n to the initial value with the result that temperature T is accordingly reduced. However, the temperature control step and the gas flow rate control step may be executed in a manner opposite to the case illustrated in FIG. 3. In this case, pressure P is increased to increase the adsorption amount n in the pressure control step, and in the gas flow rate control step, the gas flow rate is controlled to thereby reduce the adsorption amount n to the initial value with the result that temperature T is accordingly increased. Therefore, also in this case, it is possible to obtain the information for adsorption isostere creation indicated by Expression (1").

In the method of measuring information for adsorption isostere creation according to the second embodiment, on the same grounds as in the case of the method of measuring information for adsorption isostere creation according to the first embodiment, the number of times the pressure control step and the gas flow rate control step are repeated alternately needs to be set to at least two, it is preferred that the number be set to at least three, and more preferably, at least five. Further, it is preferred that the upper limit of the repetition number be set to 100 times or smaller.

Further, in the method of measuring information for adsorption isostere creation according to the second embodiment, in the same manner as in the first embodiment, the gas flow rate-basis feedback control is performed instead of the weight-basis feedback control when the measurement data necessary for the creation of the adsorption isostere is obtained. Therefore, the method of measuring information for adsorption isostere creation according to the second embodiment also allows more precise feedback control to be performed than the method disclosed in Patent Document 1, and hence the accuracy of the measurement data necessary for the creation of the adsorption isostere is higher with the result that the accuracy of the adsorption heat and the adsorption isostere determined based on the measurement data is also higher.

As the above-mentioned substance to be measured used in the method of measuring information for adsorption isostere creation according to the first embodiment or the second embodiment, any kinds of substance may be used as long as the substance generates the gas adsorption/degassing reaction. Specific examples of the substance to be measured include a normal bulk substance, a fibrous substance and an aggregate thereof, a powdered substance and an aggregate thereof, a substance having a rough surface, and a porous substance. However, it is particularly preferred that the substance to be measured be the porous substance an adsorption characteristic of which is more important as the characteristic of the substance.

There is no particular limitation on the gas of specific composition used for the measurement of the information for adsorption isostere creation, and a known gas that takes a gaseous form in a measurement temperature range and a measurement pressure range may be used. Specific examples of the gas of specific composition include a gas formed of one kind of component, such as an oxygen gas, a nitrogen gas, and a rare gas, and a gas formed of two kinds of components, such as an air containing oxygen and nitrogen as main components.

There is no particular limitation on the feedback control performed in the method of measuring information for adsorption isostere creation according to the first embodiment and in the method of measuring information for adsorption isostere creation according to the second embodiment, and a known feedback control may be used, but it is preferred that proportional-integral-derivative (PID) control be used from the viewpoint of performing more accurate feedback control.

[Adsorption Isostere Creation Method and Adsorption Heat Calculation Method]

There is no particular limitation on a purpose of using the information for adsorption isostere creation, but usually the information for adsorption isostere creation may be used to create the adsorption isostere of the substance to be measured and calculate the adsorption heat. It is preferred that a computer is used for the creation of the adsorption isostere as illustrated in FIG. 1C as an example and the calculation of the adsorption heat based on the Clapeyron-Clausius equation indicated by Expression (3) below.

$$q_{st} = R\left[\frac{\partial \ln P}{\partial (1/T)}\right]_n \quad (3)$$

In Expression (3), $q_{st}$ represents an isosteric adsorption heat, P represents an internal pressure, T represents an internal temperature, and R represents a gas constant. In addition, the internal pressure P and the internal temperature T indicated in the right side of Expression (3) becomes clear from the information for adsorption isostere creation, and hence the isosteric adsorption heat $q_{st}$ indicated in the left side of Expression (3) can be calculated.

[Computer Program]

The above-mentioned method of measuring information for adsorption isostere creation according to the first embodiment, the above-mentioned method of measuring information for adsorption isostere creation according to the second embodiment, and an adsorption isostere creation method and an adsorption heat calculation method using those methods of measuring information for adsorption isostere creation may also be provided in the form of a computer program described in a known programming language which can be executed by a computer.

In this case, a computer program according to the first embodiment for executing the method of measuring information for adsorption isostere creation according to the first embodiment causes a computer to execute at least: (A) the temperature control step; (B) the gas flow rate control step; and (E) an adsorption isostere creation-purpose information measurement step of obtaining the information for adsorption isostere creation, which is a set of at least three measurement information items each containing a pair of one pressure value and one temperature value, by measuring at least three information items selected from the virtual measurement information group of at least three information items each containing a pair of one pressure value and one temperature value indicated by Expression (1') described above when pressure and temperature inside the container are changed by repeating (A) the temperature control step and (B) the gas flow rate control step alternately at least twice.

A computer program according to the second embodiment for executing the method of measuring information for adsorption isostere creation according to the second embodiment causes a computer to execute at least: (C) the pressure control step; (D) the gas flow rate control step; and (F) an adsorption isostere creation-purpose information measurement step of obtaining the information for adsorption isostere creation, which is a set of at least three measurement information items each containing a pair of one pressure value and one temperature value, by measuring at least three information items selected from the virtual measurement information group of at least three information items each containing a pair of one pressure value and one temperature value indicated by Expression (1") described above when pressure and temperature inside the container are changed by repeating (C) the temperature control step and (D) the gas flow rate control step alternately at least twice.

It is particularly preferred that the computer program according to either of the first embodiment and the second embodiment further cause the computer to execute at least one of: an adsorption isostere creation step of creating the adsorption isostere of the substance to be measured by using the information for adsorption isostere creation; and an adsorption heat calculation step of calculating the adsorption heat of the substance to be measured.

[Measurement System]

There is no particular limitation on a configuration of a measurement system that can be used for executing the above-mentioned method of measuring information for adsorption isostere creation according to the first embodiment and the above-mentioned method of measuring information for adsorption isostere creation according to the second embodiment as long as the measurement system includes a configuration that can execute those measurement methods, but it is particularly preferred that the measurement system include the following configuration.

That is, as such a measurement system, it is preferred that the measurement system include at least: a container; a gas supply channel connected to the container, for supplying a gas of specific composition from the outside of the container to the inside of the container; a gas discharge channel connected to the container, for discharging the gas of specific composition inside the container from the inside of the container to the outside of the container; a gas supply amount control unit provided on the gas supply channel, for controlling a gas supply amount of the gas of specific composition, which is supplied from the outside of the container to the inside of the container; a gas discharge amount control unit provided on the gas discharge channel, for controlling a gas discharge amount of the gas of specific composition, which is discharged from the inside of the container to the outside of the container; a temperature control unit for controlling temperature inside the container; a pressure control unit for controlling pressure inside the container; a gas supply amount measuring unit provided on the gas supply channel, for measuring the gas supply amount; a gas discharge amount measuring unit provided on the gas discharge channel, for measuring the gas discharge amount; a temperature measuring unit for measuring temperature inside the container; a pressure measuring unit for measuring pressure inside the container; and a parameter control unit including a function of controlling at least one kind of parameter value selected from the group consisting of the gas supply amount, the gas discharge amount, temperature, and pressure, based on at least one kind of input value selected from the group consisting of: a measurement value group measured by at least one measuring unit selected from the group consisting of the gas supply amount measuring unit, the gas discharge amount measuring unit, the temperature measuring unit, and the pressure measuring unit; and a setting value group of at least one selected from the group consisting of the gas supply amount, the gas discharge amount, a temperature variation, and a pressure variation that are set in advance.

"The measurement system" used in this specification means a system including the container in which the substance to be measured is located and other component parts. Here, all the other component parts may be provided physically unitarily with an apparatus main body part including the container, or at least a portion of the other component parts may be provided physically separately from the apparatus main body part including the container. However, if the portion of the other component parts is provided physically separately from the apparatus main body part including the container, the portion of the other component parts which is provided physically separately from a measurement apparatus main body part is connected to the measurement apparatus main body part at the time of using the measurement system in order to enable the execution of at least one of the method of measuring information for adsorption isostere creation according to the first embodiment and the method of measuring information for adsorption isostere creation according to the second embodiment.

If the method of measuring information for adsorption isostere creation according to the first embodiment is executed, a parameter control unit includes at least a function of executing (A) the temperature control step and (B) the gas flow rate control step. Further, if the method of measuring information for adsorption isostere creation according to the second embodiment is executed, the parameter control unit includes at least a function of executing (C) the pressure control step and (D) the gas flow rate control step. Note that the parameter control unit may be provided inside a device (for example, personal computer) connected externally to the measurement apparatus main body.

The measurement apparatus may include: a recording unit including at least a function of recording the information for adsorption isostere creation, which is a set of at least three measurement information items each containing a pair of one pressure value and one temperature value and which is obtained by measuring at least three information items selected from the virtual measurement information group of at least three information items each containing a pair of one pressure value and one temperature value indicated in Expression (1') or Expression (1"), when (A) the temperature control step and (B) the gas flow rate control step or (C) the pressure control step and (D) the gas flow rate control step are repeatedly executed alternately; a data processing unit for creating the adsorption isostere and calculating the adsorption heat based on the information for adsorption isostere creation recorded in the recording unit; and a display unit for displaying results of the data processing. Further, the recording unit, the data processing unit, and the display unit may be substituted by a device (for example, personal computer and liquid crystal display) connected externally to the measurement apparatus main body.

Figure 4:
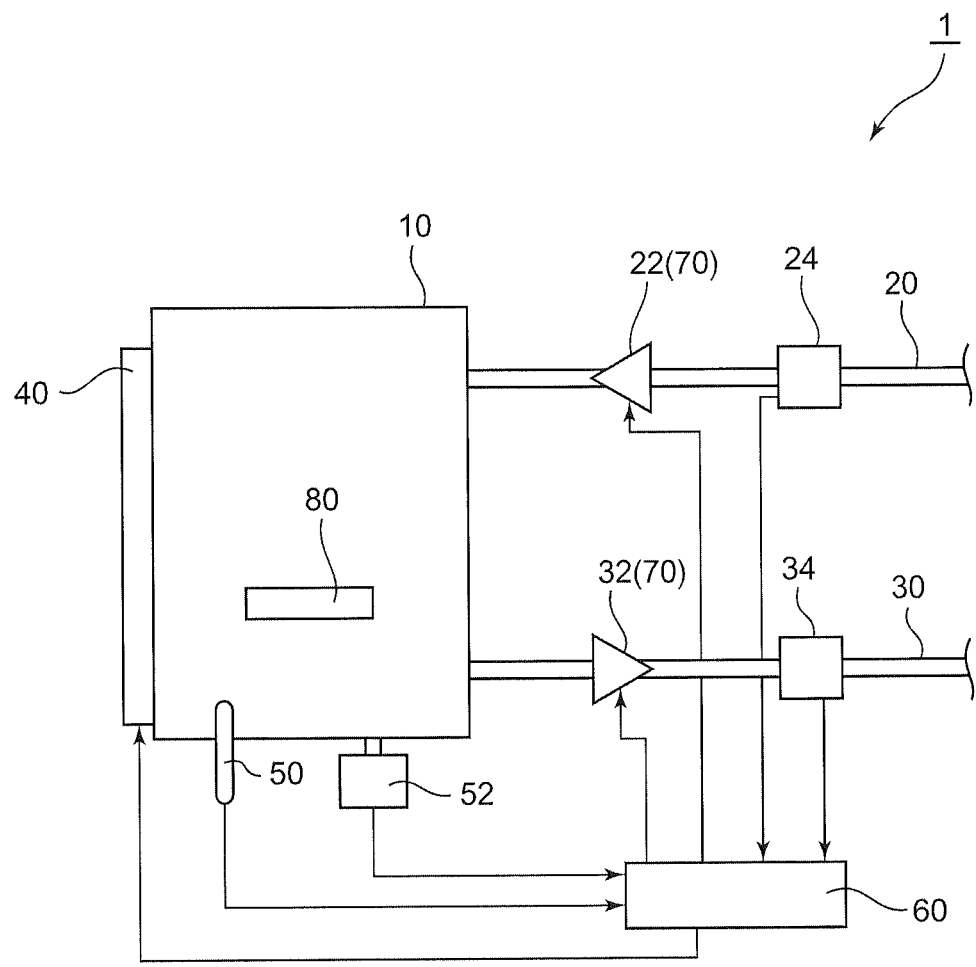
FIG. 4 is an outline schematic diagram illustrating an example of a measurement system used for the method of measuring information for adsorption isostere creation according to the first or second embodiment of the present invention.

FIG. 4 is an outline schematic diagram illustrating an example of the measurement system used for the method of measuring information for adsorption isostere creation according to the first embodiment or the second embodiment. A measurement system 1 illustrated in FIG. 4 includes a container 10, a gas supply channel 20 connected to the container 10, a flow rate regulating valve (gas supply amount control unit) 22 and a flowmeter (gas supply amount measuring unit) 24 that are provided on the gas supply channel 20, a gas discharge channel 30, a flow rate regulating valve (gas discharge amount control unit) 32 and a flowmeter (gas discharge amount measuring unit) 34 that are provided on the gas discharge channel 30, a temperature control unit 40 for controlling temperature inside the container 10, a temperature measuring unit 50 for measuring temperature inside the container 10, a pressure measuring unit 52 for measuring pressure inside the container 10, and a parameter control unit 60.

The flow rate regulating valves 22 and 32 include a function of a pressure control unit 70 for controlling pressure inside the container 10. The parameter control unit 60 is connected to the flowmeters 24 and 34, the temperature measuring unit 50, and the pressure measuring unit 52. A measurement value measured by each of those units is transmitted to the parameter control unit 60. The parameter control unit 60 is connected to the flow rate regulating valves 22 and 32 including the function of the pressure control unit 70 and to the temperature control unit 40. In addition, the parameter control unit 60 can transmit a control signal for controlling an operating state of each of those units thereto. The parameter control unit 60 may include an internal memory for recording at least one setting value selected from the group consisting of the gas supply amount, the gas discharge amount, the temperature variation, and the pressure variation, or may be connected to an external device (not shown in FIG. 4) such as a computer so that the setting value can be transmitted from the outside.

An end of the gas supply channel 20 opposite to an end connected to the container 10 may be connected to a cylinder (not shown in FIG. 4) filled with a gas other than an air, such as a hydrogen gas or a nitrogen gas, or to a gas supply source (not shown in FIG. 4) for supplying the gas. An end of the gas discharge channel 30 opposite to an end connected to the container 10 may be connected to a gas collecting unit (not shown in FIG. 4) for collecting the gas discharged from the inside of the container 10.

In the measurement of the information for adsorption isostere creation, first, a substance to be measured 80 is located inside the container 10, and a gas inside of the container 10 is replaced with the gas supplied from the gas supply channel 20. In this state, in the case of measuring the information for adsorption isostere creation indicated in Expression (1'), the flow rate regulating valves 22 and 32 and the temperature control unit 40 are controlled to thereby measure temperature T and pressure P while repeating the temperature control step and the gas flow rate control step alternately. In the example of FIG. 4, the temperature control unit 40 and the temperature measuring unit 50 are provided in positions remote from the substance to be measured 80, but may be located in positions in contact with or in proximity to the substance to be measured 80. In this case, at least one of the heating and the cooling of the substance to be measured 80 can be performed quickly, and the result of measuring the substance to be measured 80 can also be fed back to the parameter control unit 60 quickly. Accordingly, the measurement time can be further reduced.

What is claimed is:

1. A method of measuring information for adsorption isostere creation, comprising:

changing pressure and temperature inside a container having a fixed capacity, which is filled with a gas of specific composition and in which a substance to be measured is located, by repeating the following steps alternately at least twice, the following steps including:

(i) a first control step of controlling one of temperature and pressure inside the container for said one of temperature and pressure to be changed by a predetermined variation in a condition of the other of temperature and pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of said one of temperature and pressure; and (ii) a second control step of controlling a gas flow rate for an adsorption amount of the gas of specific composition with respect to the substance to be measured, which has been changed by execution of the first control step, to become the same as an adsorption amount of the gas of specific composition with respect to the substance to be measured, which is obtained before the execution of the first control step, in a condition of said one of temperature and pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the first control step is executed; and obtaining the information for adsorption isostere creation, which is a set of at least three measurement information items each containing a pair of one pressure value and one temperature value, by measuring at least three information items selected from a virtual measurement information group of at least three information items each containing a pair of one pressure value and one temperature value indicated by:

$$[T(O), P(O)] + \sum_{a=1}^{n} [T(a), P(a)]$$

where T(0) represents a temperature inside the container, which is measured before first execution of one of the control steps executed in a constant pressure, T(a) represents a temperature inside the container, which is measured at at least one time point within a time period between a-th execution and (a+1)-th execution of said one of the control steps, P(0) represents a pressure inside the container, which is measured before first execution of the other of control steps executed in a constant temperature, P(a) represents a pressure inside the container, which is measured at at least one time point within a time period between a-th execution and (a+1)-th execution of the other of the control steps, "a" represents an integer equal to or larger than 1, and "n" represents an integer equal to or larger than 2.

2. The method of measuring information for adsorption isostere creation according to claim 1, wherein: the information for adsorption isostere creation is measured by a measurement system, the measurement system comprising:
   the container;
   a gas supply channel connected to the container, for supplying the gas of specific composition from the outside of the container to the inside of the container;
   a gas discharge channel connected to the container, for discharging the gas of specific composition inside the container from the inside of the container to the outside of the container;
   a gas supply amount control unit provided on the gas supply channel, for controlling the gas supply amount of the gas of specific composition, which is supplied from the outside of the container to the inside of the container;
   a gas discharge amount control unit provided on the gas discharge channel, for controlling the gas discharge amount of the gas of specific composition, which is discharged from the inside of the container to the outside of the container;
   a temperature control unit for controlling temperature inside the container;
   a pressure control unit for controlling pressure inside the container;
   a gas supply amount measuring unit provided on the gas supply channel, for measuring the gas supply amount;
   a gas discharge amount measuring unit provided on the gas discharge channel, for measuring the gas discharge amount;
   a temperature measuring unit for measuring temperature inside the container;
   a pressure measuring unit for measuring pressure inside the container; and
   a parameter control unit comprising a function of controlling at least one kind of parameter value selected from the group consisting of the gas supply amount, the gas discharge amount, temperature, and pressure, based on at least one kind of input value selected from the group consisting of: a measurement value group measured by at least one measuring unit selected from the group consisting of the gas supply amount measuring unit, the gas discharge amount measuring unit, the temperature measuring unit, and the pressure measuring unit; and a setting value group of at least one selected from the group consisting of the gas supply amount, the gas discharge amount, a temperature variation, and a pressure variation that are set in advance; in which:
   the parameter control unit comprises a function of executing the first control step and the second control step.

3. The method of measuring information for adsorption isostere creation according to claim 1, wherein the substance to be measured comprises a porous substance.

4. An adsorption isostere creation method, comprising using the information for adsorption isostere creation obtained by the method of measuring information for adsorption isostere creation according to claim 1, to thereby create an adsorption isostere of the substance to be measured.

5. An adsorption heat calculation method, comprising using the information for adsorption isostere creation obtained by the method of measuring information for adsorption isostere creation according to claim 1, to thereby calculate an adsorption heat of the substance to be measured.

6. A measurement system, comprising:
   a container;
   a gas supply channel connected to the container, for supplying a gas of specific composition from the outside of the container to the inside of the container;
   a gas discharge channel connected to the container, for discharging the gas of specific composition inside the container from the inside of the container to the outside of the container;
   a gas supply amount control unit provided on the gas supply channel, for controlling a gas supply amount of the gas of specific composition, which is supplied from the outside of the container to the inside of the container;
   a gas discharge amount control unit provided on the gas discharge channel, for controlling a gas discharge amount of the gas of specific composition, which is discharged from the inside of the container to the outside of the container;
   a temperature control unit for controlling temperature inside the container;
   a pressure control unit for controlling pressure inside the container;
   a gas supply amount measuring unit provided on the gas supply channel, for measuring the gas supply amount;
   a gas discharge amount measuring unit provided on the gas discharge channel, for measuring the gas discharge amount;
   a temperature measuring unit for measuring temperature inside the container;
   a pressure measuring unit for measuring pressure inside the container;
   a parameter control unit comprising a function of controlling at least one kind of parameter value selected from the group consisting of the gas supply amount, the gas discharge amount, temperature, and pressure, based on at least one kind of input value selected from the group consisting of: a measurement value group measured by at least one measuring unit selected from the group consisting of the gas supply amount measuring unit, the gas discharge amount measuring unit, the temperature measuring unit, and the pressure measuring unit; and a setting value group of at least one selected from the group consisting of the gas supply amount, the gas discharge amount, a temperature variation, and a pressure variation that are set in advance; and a recording unit for recording at least one kind of measurement value selected from the measurement value group, in which:

the parameter control unit includes a function of repeating the following steps alternately at least twice, the following steps comprising:

(i) a first control step of controlling one of temperature and pressure inside the container for said one of temperature and pressure to be changed by a predetermined variation in a condition of the other of temperature and pressure inside the container being maintained constant, by performing feedback control on at least one gas flow rate selected from the group consisting of a gas supply amount of the gas of specific composition, which is supplied from the outside of the container to the inside of the container, and a gas discharge amount of the gas of specific composition, which is discharged from the inside of the container to the outside of the container, based on a result of measuring pressure inside the container, a result of measuring temperature inside the container, and the variation of said one of temperature and pressure; and (ii) a second control step of controlling a gas flow rate for an adsorption amount of the gas of specific composition with respect to the substance to be measured, which has been changed by execution of the first control step, to become the same as an adsorption amount of the gas of specific composition with respect to the substance to be measured, which is obtained before the execution of the first control step, in a condition of said one of temperature and pressure inside the container being maintained constant, by performing feedback control on the at least one gas flow rate selected from the group consisting of the gas supply amount of the gas of specific composition, which is supplied from the outside of the container to the inside of the container, and the gas discharge amount of the gas of specific composition, which is discharged from the inside of the container to the outside of the container, based on a result of measuring the gas flow rate and a result of measuring a total amount of one of the gas of specific composition, which is newly supplied to the inside of the container, and the gas of specific composition, which is newly discharged from the inside of the container, when the first control step is executed; and the recording unit includes a function of, in a process from before the first control step being executed to the first control step and the second control step being alternately executed, recording information for adsorption isostere creation, which is a set of at least three measurement information items each containing a pair of one pressure value and one temperature value and which is obtained by measuring at least three information items selected from a virtual measurement information group of at least three information items each containing a pair of one pressure value and one temperature value indicated by:

$$[T(O), P(O)] + \sum_{a=1}^{n} [T(a), P(a)]$$

where $T(0)$ represents a temperature inside the container, which is measured before first execution of one of the control steps executed in a constant pressure, $T(a)$ represents a temperature inside the container, which is measured at at least one time point within a time period between a-th execution and (a+1)-th execution of said one of the control steps, $P(0)$ represents a pressure inside the container, which is measured before first execution of the other of control steps executed in a constant temperature, $P(a)$ represents a pressure inside the container, which is measured at at least one time point within a time period between a-th execution and (a+1)-th execution of the other of the control steps, "a" represents an integer equal to or larger than 1, and "n" represents an integer equal to or larger than 2.

7. An adsorption isostere creation method, comprising using the information for adsorption isostere creation obtained by the method of measuring information for adsorption isostere creation according to claim 2, to thereby create an adsorption isostere of the substance to be measured.

8. An adsorption isostere creation method, comprising using the information for adsorption isostere creation obtained by the method of measuring information for adsorption isostere creation according to claim 3, to thereby create an adsorption isostere of the substance to be measured.

9. An adsorption heat calculation method, comprising using the information for adsorption isostere creation obtained by the method of measuring information for adsorption isostere creation according to claim 2, to thereby calculate an adsorption heat of the substance to be measured.

10. An adsorption heat calculation method, comprising using the information for adsorption isostere creation obtained by the method of measuring information for adsorption isostere creation according to claim 3, to thereby calculate an adsorption heat of the substance to be measured.

* * * * *